United States Patent [19]
Martin et al.

[11] Patent Number: 5,969,139
[45] Date of Patent: Oct. 19, 1999

[54] ACRIDINE DERIVATIVES

[75] Inventors: Joseph Armstrong Martin, Harpenden; Bradley Stuart Sherborne, Welwyn Garden City, both of United Kingdom; Gareth Mark Taylor, Munich, Germany

[73] Assignee: Hoffmann-La Roche Inc., Nutley, N.J.

[21] Appl. No.: 08/906,929

[22] Filed: Aug. 6, 1997

[30] Foreign Application Priority Data

Aug. 7, 1996 [GB] United Kingdom .................. 9616565
Apr. 18, 1997 [GB] United Kingdom .................. 9707695

[51] Int. Cl.⁶ .......................................... C07D 219/02
[52] U.S. Cl. ..................................... 546/102; 546/104
[58] Field of Search .................... 514/297, 332, 514/454; 546/103, 104, 268.1, 282.7; 549/388

[56] References Cited

U.S. PATENT DOCUMENTS 3,414,587 12/1968 Lehr et al. ............................ 260/335
3,454,577  7/1969 Lehr et al. ............................ 260/279
3,539,590 11/1970 Oftedahl ............................... 260/335

FOREIGN PATENT DOCUMENTS 0 524041  1/1993  European Pat. Off. .
0 539153  4/1993  European Pat. Off. .
0 539154  4/1993  European Pat. Off. .
0 617 046  9/1994  European Pat. Off. .
2003148  7/1971  Germany .
WO 94/08966  4/1994  WIPO .

OTHER PUBLICATIONS

N. Martin, et al, Synthesis and Conformational Study of Acridine Derivatives Related to 1,4–Dihydropyridines, J. Heterocyclic Chem., vol. 32, pp. 235–238 (1995).

J.V. Greenhill, The Reactions with Aldehydes of Enaminones Derived from Dimedone, J. Chem. Soc., pp. 2699–2703 (1971).

B. Loev. et al., "Hantzsch–Type" Dihydropyridine Hypotensive Agents 3. J. Med. Chem., vol. 17 (9) pp. 956–965 (1974).

English Abstract for Document B1 (1993).

Chemical Abstracts, vol. 120, No. 25, Abstract No. 323197, Cremlyn, R.J., et al., Chlorosulfonation of 9–aryl 3,3,6,6–tetramethyloctahydroxanthen–1,8–diones, (1994) and Phosphorus, Sulfur Silicon Relat. Elem., vol. 81(1–4) pp. 73–82, Univ. of Hertfordshire; Div. Chem. Sci. (1993).

Chemical Abstracts, vol. 80, No. 9, Abstract No. 047781, Lemba J., et al., Condensation of 5–methylcyclohexane–1, 3–dione with aldehydes (1974) and Latv. PSR Zinat. Akad. Vestis, Kim. Ser. (Lzakam); (5) pp. 598–604 (1973).

Chemical Abstracts, vol. 77, No. 21, Abstract No. 139733, Schneider, et al., Synthesis of Basically substituted 1,8–dioxooctahydroxanthenes 3. Reaction of dialkylaminoethyl chlorides with condensation products of glyoxylic acid (1972) and Arch. Pharm. vol. 305(7) pp. 534–538 (1972).

Chemical Abstracts, vol. 116, No. 12, Abstract No. 128215, Nagarajan, K., et al., Chemistry of dimedone structures of aldehyde–dimedone adducts (1992) and Indian J. Chem. Sect. B, 92, vol. 32B (2), pp. 73–87 (1992).

English Abstract for Document B4 (1971).

*Primary Examiner*—Johann Richter
*Assistant Examiner*—Jane C. Osweckl
*Attorney, Agent, or Firm*—George W. Johnston; William H. Epstein; Briana C. Buchholz

[57] ABSTRACT

The invention relates to new and known tricyclic dione derivatives of the general formula

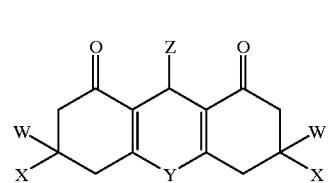

(I)

wherein

W represents hydrogen or lower alkyl;

X represents lower alkyl;

Y represents NR1;

$R^1$ represents hydrogen, lower alkyl, lower alkoxycarbonyl or lower alkoxycarbonyl-lower alkyl;

Z represents aryl or heteroaryl optionally substituted by one or more halo, cyano, nitro, lower alkyl, halo-lower alkyl, lower alkoxy, halo-lower alkoxy, $COR^2$, $OCOR^2$, $CO_2R^2$, $OR^2$, $S(O)_nR^2$, $NR^2R^3$, $N(R^4)COR^5$, Ar, Ar-lower alkyl, Het or Het-lower alkyl substituents and/or on adjacent carbon atoms by lower alkylenedioxy;

$R^2$, $R^3$, $R^4$ and $R^5$ each individually represent hydrogen, lower alkyl, Ar, Ar-lower alkyl, Het or Het-lower alkyl substituents; or $R^2$ and $R^3$ together represent the group —CH=CH—CH=CH— or —CH=N—CH=CH—;

Ar represents aryl optionally substituted by one or more halo, lower alkyl, lower alkoxy or nitro substituents;

Het represents heteroaryl optionally substituted by one or more halo, lower alkyl, lower alkoxy or nitro substituents; and n stands for 0, 1 or 2 and to their salts which are inhibitors of herpes simplex virus thymidine kinase.

9 Claims, No Drawings

ACRIDINE DERIVATIVES

BACKGROUND OF INVENTION

A number of compounds encompassed within compounds of the formula:

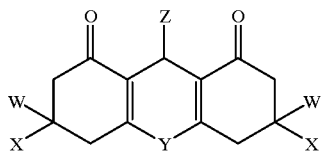

(I)

wherein
- W is hydrogen or lower alkyl;
- X is lower alkyl;
- Y is an oxygen atom or $NR^1$;
- $R^1$ is hydrogen, lower alkyl, lower alkoxycarbonyl or lower alkoxycarbonyl-lower alkyl;
- Z is either aryl or heteroaryl or aryl or heteroaryl substituted by one or more substituents selected from the group consisting of halo, cyano, nitro, lower alkyl, halo-lower alkyl, lower alkoxy, halo-lower alkoxy, $COR^2$, $OCOR^2$, $CO_2R^2$, $OR^2$, $S(O)_nR^2$, $NR^2R^3$, $N(R^4)COR^5$, Ar, Ar-lower alkyl, Het, Het-lower alkyl and on adjacent carbon atoms lower alkylenedioxy;
- $R^2$, $R^3$, $R^4$ and $R^5$ are individually hydrogen, lower alkyl, Ar, Ar-lower alkyl, Het or Het-lower alkyl substituents; or $R^2$ and $R^3$ together represent the group —CH=CH—CH=CH— or —CH=N—CH=CH—;
- Ar is aryl or aryl substituted with at least one halo, lower alkyl, lower alkoxy or nitro substituent;
- Het is heteroaryl or heteroaryl substituted by one or more halo, lower alkyl, lower alkoxy or nitro substituents; and
- n stands for 0, 1 or 2 or a salt thereof are disclosed in, inter alia, U.S. Pat. Nos. 3,414,587, 3,454,577 and 3,539,590, European Patent Publications Nos. 524 041, 369 762, 539,154 and 539,153, German Offenlegungsschrift No. 2,003,148, PCT Patent Publication No. WO 9408966 and B. Loev et al., J. Med. Chem., 1974, 17(9), 956–965 and are reported therein to have activities as anthelmintics, antibacterials, antihypertensives or agents for the treatment of urinary incontinence. No mention is made in these references with respect to their inhibition of herpes simplex virus (HSV) thymidine kinase (TK).

SUMMARY OF INVENTION

It has now surprisingly been found in accordance with the present invention that the compounds of formula I inhibit HSV TK and can accordingly be used in the treatment and prevention of infections caused by herpes simplex virus. Accordingly, one aspect of the invention is directed to the use of compounds of formula I hereinbefore in the treatment and prophylaxis of infections caused by herpes simplex virus and, respectively, for the production of corresponding medicaments.

Another aspect of this invention comprises the novel compounds included with the compounds of formula I. These novel compounds are compounds of the formula:

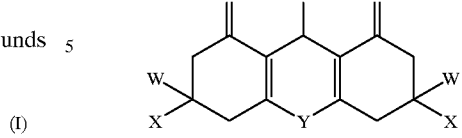

(IA)

wherein
- W is hydrogen or lower alkyl;
- X is lower alkyl;
- Y is oxygen or $NR^1$;
- $R^1$ is hydrogen, lower alkyl, lower alkoxycarbonyl or lower alkoxycarbonyl-lower alkyl;
- Z' is either aryl or heteroaryl, where the aryl and hetaryl:
  (a) are substituted with at least two substituents selected from the group consisting of halo, cyano, nitro, lower alkyl, halo-lower alkyl, lower alkoxy, halo-lower alkoxy, $COR^2$, $OCOR^2$, $CO_2R^2$, $OR^2$, $S(O)_nR^2$, $NR^2R^3$, $N(R^4)COR^5$, Ar, Ar-lower alkyl, Het, Het-lower alkyl and on adjacent carbon atoms lower alkylenedioxy; or
  (b) are substituted with at least one substituent selected from the group consisting of OHet, O-lower alkyl-Het, $N(R^4)COHet$ and $NR^{2'}R^{3'}$ wherein $R^{2'}$ and $R^{3'}$ taken together form —CH=CH—CH=CH— or —CH=N—CH=CH—;
- $R^2$, $R^3$, $R^4$ and $R^5$ each individually are hydrogen, lower alkyl, Ar, Ar-lower alkyl, Het or Het-lower alkyl substituents; or $R^2$ and $R^3$ taken together form —CH=CH—CH=CH— or —CH=N—CH=CH—;
- Ar is aryl or aryl substituted with at least one halo, lower alkyl, lower alkoxy or nitro substituent;
- Het is heteroaryl or heteroaryl substituted with at least one halo, lower alkyl, lower alkoxy or nitro substituent; and
- n is 0, 1 or 2, with the proviso that a) when W and X is methyl and Y is an oxygen, then Z is not 2,4-dihydroxy-phenyl, 3,4-dimethoxy-phenyl, 4-benzyloxy-3,5-dimethoxy-phenyl, 4-hydroxy-3,5-dimethoxy-phenyl, 3-hydroxy-4-methoxy-phenyl, 3,5-dichloro-2-hydroxy-phenyl, 4-hydroxy-3-methoxy-phenyl, 3,4-methylenedioxy-phenyl or 2,4,5-trimethoxy-phenyl; and
  b) when W and X is methyl and Y is —NH—; Z is not 2,5-dibenzyloxy-4-methyl-phenyl or 2,5-dihydroxy-4-methyl-phenyl.

or salts thereof.

DETAILED DESCRIPTION

In accordance with this invention we have found that the compounds of the formula:

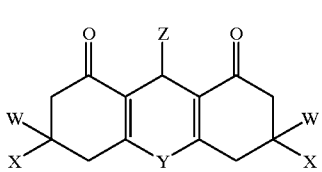

(I)

wherein
- W is hydrogen or lower alkyl;
- X is lower alkyl;

Y is an oxygen atom or NR$^1$;

R$^1$ is hydrogen, lower alkyl, lower alkoxycarbonyl or lower alkoxycarbonyl-lower alkyl;

Z is either aryl or heteroaryl or aryl or heteroaryl substituted by one or more substituents selected from the group consisting of halo, cyano, nitro, lower alkyl, halo-lower alkyl, lower alkoxy, halo-lower alkoxy, COR$^2$, OCOR$^2$, CO$_2$R$^2$, OR$^2$, S(O)$_n$R$^2$, NR$^2$R$^3$, N(R$^4$)COR$^5$, Ar, Ar-lower alkyl, Het, Het-lower alkyl and on adjacent carbon atoms lower alkylenedioxy;

R$^2$, R$^3$, R$^4$ and R$^5$ are individually hydrogen, lower alkyl, Ar, Ar-lower alkyl, Het or Het-lower alkyl substituents; or R$^2$ and R$^3$ together represent the group —CH=CH—CH=CH— or —CH=N—CH=CH—;

Ar is aryl or aryl substituted with at least one halo, lower alkyl, lower alkoxy or nitro substituent;

Het is heteroaryl or heteroaryl substituted by one or more halo, lower alkyl, lower alkoxy or nitro substituents; and n stands for 0, 1 or 2 or a salt thereof are useful in treating or preventing infections caused by herpes simplex virus in humans.

In accordance with another embodiment of this invention it has been found that compounds of the formula:

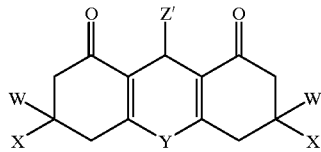

(IA)

wherein

W is hydrogen or lower alkyl;

X is lower alkyl;

Y is oxygen or NR$^1$;

R$^1$ is hydrogen, lower alkyl, lower alkoxycarbonyl or lower alkoxycarbonyl-lower alkyl;

Z' is either aryl or heteroaryl, where the aryl and hetearyl:
  (a) are substituted with at least two substituents selected from the group consisting of halo, cyano, nitro, lower alkyl, halo-lower alkyl, lower alkoxy, halo-lower alkoxy, COR$^2$, OCOR$^2$, CO$_2$R$^2$, OR$^2$, S(O)$_n$R$^2$, NR$^2$R$^3$, N(R$^4$)COR$^5$, Ar, Ar-lower alkyl, Het, Het-lower alkyl and on adjacent carbon atoms lower alkylenedioxy; or
  (b) are substituted with at least one substituent selected from the group consisting of OHet, O-lower alkyl-Het, N(R$^4$)COHet and NR$^{2'}$R$^{3'}$ wherein R$^{2'}$ and R$^{3'}$ taken together form —CH=CH—CH=CH— or —CH=N—CH=CH—;

R$^2$, R$^3$, R$^4$ and R$^5$ each individually are hydrogen, lower alkyl, Ar, Ar-lower alkyl, Het or Het-lower alkyl substituents; or R$^2$ and R$^3$ taken together form —CH=CH—CH=CH— or —CH=N—CH=CH—;

Ar is aryl or aryl substituted with at least one halo, lower alkyl, lower alkoxy or nitro substituent;

Het is heteroaryl or heteroaryl substituted with at least one halo, lower alkyl, lower alkoxy or nitro substituent; and n is 0, 1 or 2, with the proviso that a) when W and X is methyl and Y is an oxygen, then Z is not 2,4-dihydroxy-phenyl, 3,4-dimethoxy-phenyl, 4-benzyloxy-3,5-dimethoxy-phenyl, 4-hydroxy-3,5-dimethoxy-phenyl, 3-hydroxy-4-methoxy-phenyl, 3,5-dichloro-2-hydroxy-phenyl, 4-hydroxy-3-methoxy-phenyl, 3,4-methylenedioxy-phenyl or 2,4,5-trimethoxy-phenyl; and b) when W and X is methyl and Y is —NH—, then Z is not 2,5-dibenzyloxy-4-methyl-phenyl or 2,5-dihydroxy-4-methyl-phenyl;

or a salt thereof included within compounds on the formula I are novel and can be used as prophylactics and in the treatment of infections caused by herpes simplex virus in humans.

As used herein, the term "aryl" means a monocyclic or polycyclic aromatic group, preferably containing 5 to 14 carbon atoms, especially phenyl or naphthyl and particularly phenyl. The term "heteroaryl" means a 5- or 6-membered N-, S- or O-containing heteroaromatic group which may be benz-fused, e.g. pyridyl, thienyl, furyl, pyrimidinyl, quinolyl, benzofuranyl and the like. The preferred heteroaryl can be a 5-or 6-membered heteroaromatic carbon atom containing ring which contains within the ring from 1 to 3 hetero atoms selected from the group consisting of nitrogen, sulfur and or oxygen.

Also as used herein, the term "lower" means that the group described contains from 1 to 7, preferably 1 to 4, carbon atoms. Lower alkyl and lower alkoxy groups can be straight-chain or branched, such as methyl, ethyl, n-propyl, isopropyl, n-butyl and tert.butyl and, respectively, methoxy, ethoxy, n-propoxy, isopropoxy, n-butoxy and tert.butoxy. Trifluoromethyl is an example of a halo-lower alkyl group and trifluoromethoxy is an example of a halo-lower alkoxy group. Methylenedioxy and ethylenedioxy are examples of lower alkylenedioxy groups. Lower alkoxycarbonyl can be, for example, methoxycarbonyl, ethoxycarbonyl, n-propoxycarbonyl, isopropoxycarbonyl and the like. The term "halo" means fluoro, chloro, bromo or iodo.

In the aforementioned use of the compounds of formula I there are preferred those compounds in which W and X represent methyl. Also preferred in the aforementioned use are compounds of formula I in which Y represents NR$^1$ wherein R$^1$ represents hydrogen, as well as those in which Z represents aryl or heteroaryl substituted by:
  i) two or more halo, cyano, nitro, lower alkyl, halo-lower alkyl, lower alkoxy, halo-lower alkoxy, COR$^2$, OCOR$^2$, CO$_2$R$^2$, OR$^2$, S(O)$_n$R$^2$, NR$^2$R$^3$, N(R$^4$)COR$^5$, Ar, Ar-lower alkyl, Het or Het-lower alkyl substituents and/or on adjacent carbon atoms by lower alkylenedioxy; or by
  ii) one substituent from OHet, O-lower alkyl-Het, N(R$^4$)COHet and NR$^{2'}$R$^{3'}$ in which R$^{2\ '}$ and R$^{3\ '}$ together represent —CH=CH—CH=CH— or —CH=N—CH=CH—.

In one especially preferred embodiment Z represents phenyl substituted by Ar, OR$^2$ or S(O)$_n$R$^2$ in the meta-position and by halo, cyano or nitro in the para-position, particularly by phenyl, benzyloxy, phenoxy, pyridyloxy, phenylthio or pyridylthio in the meta-position and by chlorine, bromine, fluorine, cyano or nitro in the para-position. In another especially preferred embodiment Z represents phenyl monosubstituted, preferably in the meta-position, by OHet, O-lower alkyl-Het or NHCOHet in which Het represents pyridyl.

The invention is concerned in a further aspect with compounds of formula I and their salts per se which are still novel. These are compounds of formula I in which W, X, Y, R$^1$, R$^2$, R$^3$, R$^4$, R$^5$, Ar, Het and n are as defined above and Z represents aryl or heteroaryl substituted by:
  i) two or more halo, cyano, nitro, lower alkyl, halo-lower alkyl, lower alkoxy, halo-lower alkoxy, COR$^2$, OCOR$^2$, $CO_2R^2$, $OR^2$, $S(O)_nR^2$, $NR^2R^3$, $N(R^4)COR^5$, Ar, Ar-lower alkyl, Het or Het-lower alkyl substituents and/or on adjacent carbon atoms by lower alkylenedioxy; or by ii) one substituent from OHet, O-lower alkyl-Het, $N(R^4)$COHet and $NR^{2'}R^{3'}$ in which $R^{2'}$ and $R^{3'}$ together represent —CH=CH—CH=CH— or —CH=N—CH=CH—; with the proviso that a) when W and X represent methyl and Y represents an oxygen atom, then Z does not represent 2,4-dihydroxy-phenyl, 3,4-dimethoxy-phenyl, 4-benzyloxy-3,5-dimethoxy-phenyl, 4-hydroxy-3,5-dimethoxy-phenyl, 3-hydroxy-4-methoxy-phenyl, 3,5-dichloro-2-hydroxy-phenyl, 4-hydroxy-3-methoxy-phenyl, 3,4-methylenedioxy-phenyl or 2,4,5-trimethoxy-phenyl; and b) when W and X represent methyl and Y represents $NR^1$ in which $R^1$ represents hydrogen, then Z does not represent 2,5-dibenzyloxy-4-methyl-phenyl or 2,5-dihydroxy-4-methyl-phenyl.

Preferred novel compounds of formula I-A are those in which W and X represent methyl. Also preferred are those in which Y represents $NR^1$ wherein $R^1$ represents hydrogen, as well as those in which Z represents phenyl substituted by Ar, $OR^2$ or $S(O)_nR^2$ in the meta-position and by halo, cyano or nitro in the para-position, particularly by phenyl, benzyloxy, phenoxy, pyridyloxy, phenylthio or pyridylthio in the meta-position and by chlorine, bromine, fluorine, cyano or nitro in the para-position. In another especially preferred embodiment Z represents phenyl monosubstituted, preferably in the meta-position, by OHet, O-lower alkyl-Het or NHCOHet in which Het represents pyridyl.

In accordance with this invention the preferred compounds of formula I-A are compounds of the formula:

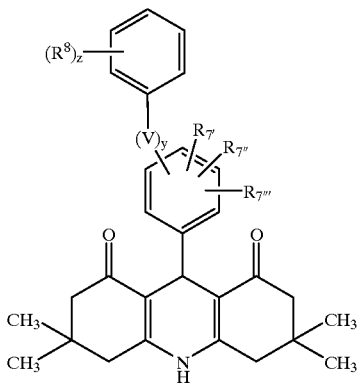

I-A₁ wherein V is —O—, —CH₂O— or —S—; $R_{7'}$, $R_{7''}$, $R_{7'''}$ and $R_8$ are individually halo, lower alkyl, hydrogen, halo-lower alkyl, lower alkoxy or nitro; with the proviso that one of $R_{7'}$, $R_{7''}$ or $R_{7'''}$ is other than hydrogen; z is an integer from 0 to 3; and y is an integer from 0 to 1, or a salt thereof.

Also preferred are compounds of the formula:

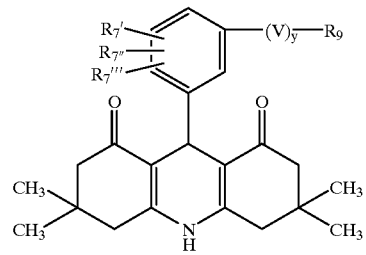

I-A₂ wherein $R_{7'}$, $R_{7''}$ and $R_{7'''}$ are independently hydrogen, lower alkyl, halo, halo-lower alkyl, lower alkoxy or nitro; V is —NHC(O)—, —S—, —O— or —O—CH₂—; $R_9$ is heteroaryl; and y is an integer from 0 to 1 or a salt thereof.

Another embodiment of this invention are compounds of the formula:

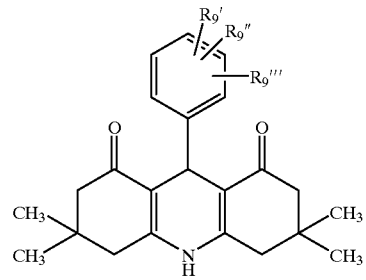

I-A₃ wherein $R_{9'}$, $R_{9''}$ and $R_{9'''}$ are individually selected from the group consisting of hydrogen, halo, cyano, nitro, lower alkyl, halo-lower alkyl and lower alkoxy, with at least two of said $R_{9'}$, $R_{9''}$ and $R_{9'''}$ being other than hydrogen, or a salt thereof.

In accordance with this invention the compounds of formulae I, I-A, IA-1, I-A2 and I-A3 can be in their salt form. Any conventional pharmaceutically acceptable salt can be used. Among the preferred salts are salts with pharmaceutically acceptable acids or bases. Basic compounds of formula I can form salts with inorganic acids, e.g. hydrohalic acids such as hydrochloric acid or hydrobromic acid, sulphuric acid, nitric acid or phosphoric acid, or with organic acids, e.g. formic acid, acetic acid, citric acid, fumaric acid, malic acid, maloic acid, succinic acid, tartaric acid, salicylic acid, methanesulphonic acid or p-toluenesulphonic acid. Acidic compounds of formula I can form salts with metals, e.g. alkali metal salts such as sodium or potassium salts or alkaline earth metal salts such as calcium or magnesium salts, with organic bases, e.g. salts with amines such as N-ethylpiperidine, procaine or dibenzylamine, or salts with basic amino acids such as salts with arginine or lysine. These salts can be formed and isolated by methods well known in the art.

Examples of particularly preferred novel compounds of formula I are:

9-(4-Chloro-3-phenoxyphenyl)-3,4,6,7,9,10-hexahydro-3,3,6,6-tetramethyl-1,8(2H,5H)-acridinedione;

9-(4-chloro-3-phenylthiophenyl)-3,4,6,7,9,10-hexahydro-3,3,6,6-tetramethyl-1,8(2H,5H)-acridinedione;

9-(6-chloro-3-biphenylyl)-3,4,6,7,9,10-hexahydro-3,3,6,6-tetramethyl-1,8(2H,5H)-acridinedione;

9-[4-chloro-3-(4-pyridyloxy)phenyl]-3,4,6,7,8,10-hexahydro-3,3,6,6-tetramethyl-1,8(2H,5H)-acridinedione;

9-[4-chloro-3-(4-pyridylthio)phenyl]-3,4,6,7,8,10-hexahydro-3,3,6,6-tetramethyl-1,8(2H,5H)-acridinedione; and 9-(3-benzyloxy-4-nitrophenyl)-3,4,6,7,8,10-hexahydro-3,3,6,6-tetramethyl-1,8(2H,5H)-acridinedione.

The invention is further concerned with a process for the manufacture of the aforementioned novel compounds, which process comprises a) for the manufacture of a compound of formula I in which Y represents an oxygen atom, reacting an aldehyde of the general formula

Z—CHO                                    (II)

wherein Z has the significance given earlier, with a cyclohexanedione derivative of the general formula (III)

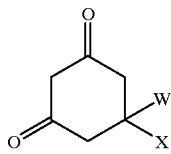

wherein W and X have the significances given earlier, or b) for the manufacture of a compound of formula I in which Y represents NR$^1$ and R$^1$ represents hydrogen, reacting an aldehyde of formula II or an acetal or hemiacetal thereof with a cyclohexanedione derivative of formula III and aqueous ammonia, or c) for the manufacture of a compound of formula I in which Y represents NR$^1$ and R$^1$ represents hydrogen, lower alkyl or lower alkoxycarbonyl-lower alkyl, reacting an aldehyde of formula II or an acetal or hemiacetal thereof with a cyclohexenone derivative of the general formula (IV)

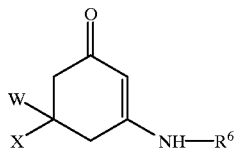

wherein W and X have the significances given earlier and R$^6$ represents hydrogen, lower alkyl or lower alkoxycarbonyl-lower alkyl, or d) for the manufacture of a compound of formula I in which Y represents NR$^1$ and R$^1$ represents lower alkoxycarbonyl, reacting a compound of formula I in which Y represents NR$^1$ and R$^1$ represents hydrogen with a lower alkyl chloroformate, or e) for the manufacture of a compound of formula I in which Z carries an amino or NHCOR$^5$ substituent, reducing a corresponding compound of formula I in which Z carries a nitro substituent and, where required, acylating the resulting compound of formula I in which Z carries an amino substituent and, if desired, forming a salt.

The reaction of an aldehyde of formula II with a cyclohexanedione derivative of formula III in accordance with embodiment a) of the process can be carried out in a manner known per se, e.g. as described in U.S. Pat. Nos. 3,414,587, 3,454,577 and 3,539,590. Thus, for example, the reaction can be carried out in an inert organic solvent, e.g. a lower alkanol, such as methanol or ethanol, an aromatic hydrocarbon, such as benzene or toluene, or a carboxylic acid, e.g. acetic acid, suitably at an elevated temperature, e.g. the reflux temperature of the reaction mixture. When a non-acidic solvent is used, an acid catalyst, e.g. a sulphonic acid, such as p-toluenesulphonic acid, is conveniently present.

Embodiment b) of the process can also be carried out in a known manner, e.g. as described by Martin et al. in J. Heterocyclic Chem. 1995, vol. 32, p. 235. For example, the reaction can be carried out in an inert organic solvent at an elevated temperature, preferably at the reflux temperature of the reaction mixture. Suitable solvents include those referred to earlier in connection with embodiment a) of the process.

Known procedures, described e.g. by Greenhill in J. Chem. Soc. (C) 1971, p. 2699, can also be used for the reaction according to embodiment c) of the process. Suitably, the reaction is effected in an inert organic solvent at an elevated temperature, especially at the reflux temperature of the reaction mixture. Typical solvents are those mentioned earlier in connection with embodiment a) of the process. The reaction is conveniently carried out in the presence of an acid, especially a hydrohalic acid, especially hydrochloric acid, when a non-acidic solvent is used.

Embodiment d) of the process is carried out in a manner known per se, conveniently by deprotonating a solution of the compound of formula (I) in an inert organic solvent, e.g. a formamide, such as dimethylformamide, with an alkali metal hydride, especially sodium hydride, at an elevated temperature, e.g. at the reflux temperature of the mixture, and then reacting with the desired lower alkyl chloroformate, e.g. methyl chloroformate, suitably at about room temperature.

Methods known per se can be used to carry out embodiment e) of the process. Thus, for example, the reduction can be carried out using hydrogen in the presence of a suitable catalyst, e.g. a palladium catalyst such as Pd/C, and in an inert organic solvent, e.g. a lower alkanol such as ethanol. Again, for example, the subsequent acylation can be performed by condensing the amine with a conventional acylating agent, e.g. an acid or one of its reactive derivatives such as an acid halide, conveniently in an inert organic solvent and in the presence of a conventional condensation agent or acid-binding agent.

The compounds of formulae (II), (III) and (IV) used as starting materials in the process provided by the invention, insofar as they are not known compounds or analogues of known compounds, can be prepared as described in the following Examples or in analogy thereto.

The pharmacological activity of the compounds of formula I can be demonstrated on the basis of the following test procedure for the inhibition of HSV-1 and HSV-2 thymidine kinase (TK):

In this test procedure, the assay mixture contains 50 mmol Tris HCl, pH 8, 5 mmol magnesium chloride, 5 mmol ATP, 0.3 mmol 3H-thymidine (50 Ci/mmol), suitably diluted enzyme preparation and various concentrations of test compounds in a total volume of 100 ml. Assays are incubated at 37° C. for 30 minutes and the reaction is terminated by immersion in a boiling water bath for 2 minutes. 85 ml aliquots from each assay are then dried on to DEAEcellulose paper discs and the unphosphorylated 3H-thymidine is removed by washing in 4 mmol ammonium formate. The radioactivity remaining bound to the discs is then measured by scintillation spectrophotometry. The degree of inhibition at each concentration of test compound is expressed as a percentage of the control reaction (100%) after subtracting a measured blank value which represents the amount of radioactivity bound to the disc from a reaction containing heat-inactivated enzymes. The IC50 value, namely the concentration of test compound which inhibits enzyme activity by 50%, is then calculated.

The results obtained in the foregoing test using representative compounds of formula I are given in the following Table:

TABLE

| Compound | Activity against HSV-1 TK IC$_{50}$ (nmol) | Activity against HSV-2 TK IC$_{50}$ (nmol) |
|---|---|---|
| A | 0.3 | 0.095 |
| B | 0.56 | 0.12 |
| C | 0.52 | 0.27 |
| D | 9.4 | 0.64 |
| E | 5.9 | 0.44 |
| F | 0.44 | 0.18 |
| G | 5.8 | 1.1 |
| H | 12 | 1.5 |
| I | 0.8 | 0.19 |
| J | 0.9 | 0.38 |
| K | 2.6 | 0.54 |

A = 9-(4-Chloro-3-phenoxyphenyl)-3,4,6,7,9,10-hexahydro-3,3,6,6-tetramethyl-1,8(2H,5H)-acridinedione.
B = 9-(4-Chloro-3-phenylthiophenyl)-3,4,6,7,9,10-hexahydro-3,3,6,6-tetramethyl-1,8(2H,5H)-acridinedione.
C = 9-(6-Chloro-3-biphenylyl)-3,4,6,7,9,10-hexahydro-3,3,6,6-tetramethyl-1,8(2H,5H)-acridinedione.
D = 9-(3,4-Dichlorophenyl)-3,4,6,7,9,10-hexahydro-3,3,6,6-tetramethyl-1,8(2H,5H)-acridinedione.
E = 9-(4-Chloro-3-fluorophenyl)-3,4,6,7,9,10-hexahydro-3,3,6,6-tetramethyl-1,8(2H,5H)-acridinedione.
F = 9-[4-Chloro-3-(1H-pyrrol-1-yl)-phenyl]-3,4,6,7,9,10-hexahydro-3,3,6,6-tetramethyl-1,8(2H,5H)-acridinedione.
G = 3,4,6,7,9,10-Hexahydro-3,3,6,6-tetramethyl-9-(3-phenoxyphenyl)-1,8(2H,5H)-acridinedione.
H = 9-(4-Bromophenyl)-3,4,6,7,9,10-hexahydro-3,3,6,6-tetramethyl-1,8(2H,5H)-acridinedione.
I = 9-[(4-Chloro-3-(4-pyridyloxy)-phenyl]-3,4,6,7,8,10-hexahydro-3,3,6,6-tetramethyl-1,8(2H,5H)-acridinedione.
J = 9-(3-Benzyloxy-4-nitrophenyl)-3,4,6,7,8,10-hexahydro-3,3,6,6-tetramethyl-1,8(2H,5H)-acridinedione.
K = 9-[4-Chloro-3-(4-pyridylthio)-phenyl]-3,4,6,7,8,10-hexahydro-3,3,6,6-tetramethyl-1,8(2H,5H)-acridinedione.

The compounds of formula I have an activity in the inhibition of HSV-1 TK and HSV-2 TK which is comparable with that of pyrimidine nucleosides disclosed in PCT Patent Publication No. WO 9603259, such as 2',5'-dideoxy-5-ethyl-5'-[(9-xanthenyl)carboxamido]uridine, which has an IC50 (nmol) of 4.2 against HSV-1 TK and an IC50 (nmol) of 0.34 against HSV-2 TK in the test described previously. However, the compounds of formula I have the advantage over these pyrimidine nucleosides in that they can be manufactured in an easier and more cost effective manner.

The compounds of formula I can be used as medicaments in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a novel compound of formula I are also an object of the present invention, as is a process for the production of such medicaments which comprises bringing one or more novel compounds and, if desired, one or more other therapeutically valuable substances into a galenical administration form together with a compatible pharmaceutical carrier.

The dosage at which the compounds of formula I can be administered can vary within wide limits and will, of course, be fitted to the individual requirements in each particular case. In general, in the case of administration to adults a daily dosage of about 1 mg to 1000 mg, preferably about 5 mg to 500 mg, should be appropriate. The daily dosage may be administered as a single dose or in divided doses. In accordance with this invention compounds of formula I as well as the novel compounds of formulae I-A, I-A$_1$, I-A$_2$ and I-A$_3$, can be utilized to treat human patients infected with herepes simplex virus. This is accomplished by administering to patients suffering from said herpes simplex virus infection a composition containing the compound of formula I or the novel compounds of formulae I-A$_1$, I-A$_2$ and I-A$_3$ in an effective amount to treat this infection. The treatment with said compound or the salts thereof will cause regression and in most cases elimination of this infection through said administration.

In accordance with a preferred embodiments of invention, the compound can be administered orally at daily dosages at 5 to 15 mg per kg body weight of said patient. The daily dose may be in one dose or in divided dosages. This daily dose should be administered for a period as long as there are signs that the infection has not regressed or been eliminated. Other methods of administration can be utilized as described above. On the other hand, these compounds can be administered prophylactically to human patients to prevent the onset of symptoms due to infection caused by herpes simplex virus. In this method, usually the patients for said prophylaxis are those who are susceptible to herpes simplex virus or who have been in contact with parties having said virus.

For prophylactic administration the compounds are administered in the aforementioned dosage forms, preferably orally, in an amount effective to prevent the infection in these patients. Generally, this dosage is administered for a period of time that is sufficient to prevent infection in a patient who is susceptible to said infection. The dosage for prophylaxis is the same as that for treatment. Generally, these dosages are administered for a period of at least 5 days and preferably no longer than 10 days. However, this may vary depending on the patient and his susceptability to the infection in question. In addition, for prophylaxis the compounds may be administered rectally or parentally. Prevention can be achieved in the same manner and using the same techniques used for treating this infection.

The following Examples illustrate the preparation of novel compounds of formula I:

EXAMPLE 1

A solution of 1.39 g of 3-amino-5,5-dimethyl-2-cyclohexen-1-one and 793 mg of 4-fluoro-3-chlorobenzaldehyde in 10 ml of absolute ethanol and 1 ml of 1M aqueous hydrochloric acid was heated at reflux under a nitrogen atmosphere for 18 hours. The cooled mixture was filtered and the residue was washed with 25 ml of cold diethyl ether. Crystallization from absolute ethanol/water gave 302 mg of 9-(4-fluoro-3-chlorophenyl)-3,4,6,7,9,10-hexahydro-3,3,6,6-tetramethyl-1,8(2H,5H)-acridinedione as a pale yellow crystalline solid of melting point 274–275° C. (decomposition).

EXAMPLE 2

A solution of 1.94 g of 5,5-dimethyl-1,3-cyclohexanedione and 1.5 ml of a 25% aqueous solution of ammonia in 10 ml of absolute ethanol was heated at reflux under an atmosphere of nitrogen for 2 hours. The mixture was cooled to room temperature and 1.588 g of 4-bromo-3-nitrobenzaldehyde were added. The mixture was then heated at reflux for a further 18 hours, cooled and filtered. The residue was washed with 25 ml of cold diethyl ether and crystallized from dimethylformamide/water to give 2.36 g of 9-(4-bromo-3-nitro-phenyl)-3,4,6,7,9,10-hexahydro-3,3,6,6-tetramethyl-1,8(2H,5H)-acridinedione as a yellow crystalline solid of melting point >300° C.

EXAMPLE 3

Reaction of 5,5-dimethyl-1,3-cyclohexanedione with 3,4-dimethylbenzaldehyde in an analogous manner to that described in Example 2 gave 9-(3,4-dimethylphenyl)-3,4,6,7,9,10-hexahydro-3,3,6,6-tetramethyl-1,8(2H,5H)-acridinedione as a yellow solid of melting point >300° C.

EXAMPLE 4

Reaction of 5,5-dimethyl-1,3-cyclohexanedione with 4-methyl-3-nitrobenzaldehyde in an analogous manner to that described in Example 2 gave 9-(4-methyl-3-nitrophenyl)-3,4,6,7,9,10-hexahydro-3,3,6,6-tetramethyl-1,8(2H,5H)-acridinedione. Crystallization from methanol gave a yellow solid of melting point >300° C.

EXAMPLE 5

Reaction of 5,5-dimethyl-1,3-cyclohexanedione with 3,4-dichlorobenzaldehyde in an analogous manner to that described in Example 2 gave 9-(3,4-dichlorophenyl)-3,4,6,7,9,10-hexahydro-3,3,6,6-tetramethyl-1,8(2H,5H)-acridinedione. Crystallization from dimethylformamide/water gave a yellow crystalline solid of melting point >300° C.

EXAMPLE 6

Reaction of 3-amino-5,5-dimethyl-2-cyclohexen-1-one with 3,4-dibromobenzaldehyde in an analogous manner to that described in Example 1 gave 9-(3,4-dibromophenyl)-3,4,6,7,9,10-hexahydro-3,3,6,6-tetramethyl-1,8(2H,5H)-acridinedione. Crystallization from absolute ethanol gave a pale yellow crystalline solid of melting point >290° C. (decomposition).

EXAMPLE 7

Reaction of 3-amino-5,5-dimethyl-2-cyclohexen-1-one with 3-bromo-4-fluorobenzaldehyde in an analogous manner to that described in Example 1 gave 9-(3-bromo-4-fluorophenyl)-3,4,6,7,9,10-hexahydro-3,3,6,6-tetramethyl-1,8(2H,5H)-acridinedione. Crystallization from absolute ethanol gave a pale yellow crystalline solid of melting point 260° C. (decomposition).

EXAMPLE 8

Reaction of 3-amino-5,5-dimethyl-2-cyclohexen-1-one with 3,4-difluorobenzaldehyde in an analogous manner to that described in Example 1 gave 9-(3,4-difluorophenyl)-3,4,6,7,9,10-hexahydro-3,3,6,6-tetramethyl-1,8(2H,5H)-acridinedione. Crystallization from absolute ethanol/water gave a pale yellow crystalline solid of melting point 270° C. (decomposition).

EXAMPLE 9

Reaction of 3-amino-5,5-dimethyl-2-cyclohexen-1-one with 4-chloro-3-fluorobenzaldehyde in an analogous manner to that described in Example 1 gave 9-(4-chloro-3-fluorophenyl)-3,4,6,7,9,10-hexahydro-3,3,6,6-tetramethyl-1,8(2H,5H)-acridinedione. Crystallization from absolute ethanol gave a yellow crystalline solid of melting point >300° C. (decomposition).

EXAMPLE 10

Reaction of 3-amino-5,5-dimethyl-2-cyclohexen-1-one with 3-benzyloxy-4-chlorobenzaldehyde in an analogous manner to that described in Example 1 gave 9-(3-benzyloxy-4-chlorophenyl)-3,4,6,7,9,10-hexahydro-3,3,6,6-tetramethyl-1,8(2H,5H)-acridinedione. Crystallization from dimethylformamide/water gave a pale yellow crystalline solid of melting point 243–244° C.

EXAMPLE 11

Reaction of 3-amino-5,5-dimethyl-2-cyclohexen-1-one with 4-chloro-3-phenoxybenzaldehyde in an analogous manner to that described in Example 1 gave 9-(4-chloro-3-phenoxyphenyl)-3,4,6,7,9,10-hexahydro-3,3,6,6-tetramethyl-1,8(2H,5H)-acridinedione. Crystallization from dimethylformamide/water gave a yellow crystalline solid of melting point 246–248° C.

EXAMPLE 12

Reaction of 3-amino-5,5-dimethyl-2-cyclohexen-1-one with 4-chloro-3-phenylthiobenzaldehyde dimethyl acetal in an analogous manner to that described in Example 1 gave 9-(4-chloro-3-phenylthio-phenyl)-3,4,6,7,9,10-hexahydro-3,3,6,6-tetramethyl-1,8(2H,5H)-acridinedione. Crystallization from dimethylformamide/water gave a yellow crystalline solid of melting point 202–204° C.

The 4-chloro-3-phenylthiobenzaldehyde dimethyl acetal used as the starting material was prepared as follows:

A solution of 312 mg of thiophenol and 85 mg of sodium hydride (80% dispersion in mineral oil) in 10 ml of diglyme was stirred at 50° C. under nitrogen for 30 minutes. 500 mg of 3-bromo-4-chlorobenzaldehyde dimethyl acetal and 500 mg of copper(I) bromide were then added and the mixture was stirred at 155–160° C. under nitrogen for 3 days. The solvent was removed under reduced pressure and the residue was taken up in 30 ml of dichloromethane. The solution was washed with 10 ml 1M aqueous potassium hydroxide solution and 10 ml of brine, and then dried over anhydrous magnesium sulphate. The solution was evaporated to dryness and the residue was purified by column chromatography on silica gel using hexane/ethyl acetate (96:4) as the eluent to give 4-chloro-3-phenylthiobenzaldehyde dimethyl acetal as a colourless oil.

EXAMPLE 13

Reaction of 3-amino-5,5-dimethyl-2-cyclohexen-1-one with 2-chloro-1,1'-biphenyl-5-carboxaldehyde in an analogous manner to that described in Example 1 gave 9-[6-chloro-3-(1,1'-biphenylyl)]-3,4,6,7,9,10-hexahydro-3,3,6,6-tetramethyl-1,8(2H,5H)-acridinedione. Crystallization from dimethylformamide/water gave a yellow crystalline solid of melting point 301–302° C. (decomposition).

The 2-chloro-1,1'-biphenyl-5-carboxaldehyde used as the starting material was prepared as follows:

(A) A solution of 5.63 g of 5-(bromomethyl)-2-chloro-1,1'-biphenyl in 60 ml of carbon tetrachloride was added dropwise over 10 minutes to a refluxing solution of 2.81 g of hexamethylenetetramine in 60 ml of carbon tetrachloride under an atmosphere of dry nitrogen. The mixture was heated at reflux for a further hour and then cooled. The resulting precipitate was filtered off and washed with petroleum ether (b.pt. 40–60° C.) to give 6.2 g of an off-white solid.

(B) A solution of 6.2 g of the solid obtained in part (A) in 60 ml of 50% aqueous acetic acid was heated at reflux for 2 hours. 8 ml of concentrated hydrochloric acid were then added and the mixture was heated at reflux for a further 10 minutes. The cooled mixture was extracted with four 50 ml portions of diethyl ether and the combined extracts were washed with 50 ml of brine, dried over anhydrous sodium sulphate and concentrated under reduced pressure to give 2.49 g of a yellow oil. Purification by column chromatography on silica gel using hexane/ethyl acetate (95:5) as the eluent gave 2-chloro-1,1'-biphenyl-5-carboxaldehyde as a white crystalline solid of melting point 84° C.

EXAMPLE 14

Reaction of 3-amino-5,5-dimethyl-2-cyclohexen-1-one with 3-cyano-4-fluorobenzaldehyde in an analogous manner to that described in Example 1 gave 5-(2,3,4,5,6,7,8,9-octahydro-3,3,6,6-tetramethyl-1,8-dioxo-1H-acridin-9-yl)-2-fluorobenzonitrile. Crystallization from ethanol gave a pale yellow-green crystalline solid of melting point 274–275° C.

The 3-cyano-4-fluorobenzaldehyde used as the starting material was prepared from 2-fluoro-5-methylbenzonitrile in a manner analogous to that described in Example 13 (A) and (B).

EXAMPLE 15

Reaction of 3-amino-5,5-dimethyl-2-cyclohexen-1-one with 4-cyano-3-nitrobenzaldehyde in an analogous manner to that described in Example 1 gave 4-(2,3,4,5,6,7,8,9-octahydro-3,3,6,6-tetramethyl-1,8-dioxo-1H-acridin-9-yl)-2-nitrobenzonitrile. Crystallization from methanol gave a yellow crystalline solid of melting point 274–275° C.

EXAMPLE 16

A solution of 330 mg of 5,5-dimethyl-3-(methylamino)-2-cyclohexen-1-one and 300 mg of 4-chloro-3-phenoxybenzaldehyde dimethyl acetal in 10 ml of absolute ethanol and 1.5 ml of 1M aqueous hydrochloric acid was heated at reflux under an atmosphere of nitrogen for 18 hours. The mixture was evaporated to dryness and the residue was washed with hexane and diethyl ether. Recrystallization from ethyl acetate/methanol gave 9-(4-chloro-3-phenoxyphenyl)-3,4,6,7,9, 10-hexahydro-3,3,6,6,10-pentamethyl-1,8(2H,5H)-acridinedione as a yellow crystalline solid of melting point 183–185° C.

EXAMPLE 17

Reaction of 5,5-dimethyl-1,3-cyclohexanedione with 2,4-dichlorobenzaldehyde in an analogous manner to that described in Example 2 gave 9-(2,4-dichlorophenyl)-3,4,6,7,9, 10-hexahydro-3,3,6,6-tetramethyl-1,8(2H,5H)-acridinedione. Crystallization from dimethylformamide/water gave a pale green crystalline solid of melting point >300° C.

EXAMPLE 18

Reaction of 5,5-dimethyl-1,3-cyclohexanedione with 3,5-dibromobenzaldehyde in an analogous manner to that described in Example 2 gave 9-(3,5-dibromophenyl)-3,4,6, 7,9, 10-hexahydro-3,3,6,6-tetramethyl-1,8(2H,5H)-acridinedione. Crystallization from dimethylformamide/water gave a yellow crystalline solid of melting point 288–290° C.

EXAMPLE 19

Reaction of 5,5-dimethyl-1,3-cyclohexanedione with 3,5-dichlorobenzaldehyde in an analogous manner to that described in Example 2 gave 9-(3,5-dichlorophenyl)-3,4,6, 7,9,10-hexahydro-3,3,6,6-tetramethyl-1,8(2H,5H)-acridinedione. Crystallization from dimethylformamide/water gave a yellow crystalline solid of melting point 288–290° C.

EXAMPLE 20

Reaction of 5,5-dimethyl-1,3-cyclohexanedione with 2,4,6-trifluorobenzaldehyde in an analogous manner to that described in Example 2 gave 9-(2,4,6-trifluorophenyl)-3,4, 6,7,9,10-hexahydro-3,3,6,6-tetramethyl-1,8(2H,5H)-acridinedione. Crystallization from methanol/water gave a yellow crystalline solid of melting point >300° C.

EXAMPLE 21

Reaction of 3-amino-5,5-dimethyl-2-cyclohexen-1-one with 4-chloro-3-(1H-pyrrol-1-yl)benzaldehyde in an analogous manner to that described in Example 1 gave 9-[4-chloro-3-(1H-pyrrol-1-yl)phenyl]-3,4,6,7,9,10-hexahydro-3,3,6,6-tetramethyl-1,8(2H,5H)-acridinedione. This product was recrystallized from dimethylformamide/water and gave a yellow crystalline solid of melting point 282–283° C. (decomposition).

The 4-chloro-3-(1H-pyrrol-1-yl)benzaldehyde used as the starting material was prepared as follows:

(A) 5.0 g of 4-chloro-3-(1H-pyrrol-1-yl)benzoic acid in 200 ml of dichloromethane were treated in succession with 3.13 ml of triethylamine and 4.33 g of 1-(3-dimethylaminopropyl)-3-ethylcarbodiimide hydrochloride (EDAC.HCl). The mixture was stirred at room temperature until it became clear and was then cooled to 0° C. and 2.21 g of N,O-dimethylhydroxylamine hydrochloride were added. The mixture was then left to come to room temperature and was stirred for a further 18 hours, washed with 1M aqueous hydrochloric acid and with brine and then dried over anhydrous magnesium sulphate. Evaporation under reduced pressure gave 5.73 g of N-methoxy-N-methyl-4-chloro-3-(1H-pyrrol-1-yl) benzamide as a viscous oil.

(B) A solution of 1.5 g of N-methoxy-N-methyl-4-chloro-3-(1H-pyrrol-1-yl)benzamide in 30 ml of anhydrous tetrahydrofuran was added drop-wise over a period of 30 minutes to a solution, pre-cooled to 0–5° C., of 237 mg of lithium aluminium hydride (98%) in 30 ml of anhydrous tetrahydrofuran. The mixture was stirred at 0–5° C. for a further 45 minutes and ther reaction was then quenched by the addition of 25 ml of saturated aqueous ammonium chloride solution and 25 ml of 50% aqueous hydrochloric acid. The mixture was then extracted with three 100 ml portions of diethyl ether and the combined extracts were dried over anhydrous magnesium sulphate. The solvents were removed under reduced pressure and the residue was purified by column chromatography on silica gel using hexane/ethyl acetate (90:10) as the eluent to give 0.84 g of 4-chloro-3-(1H-pyrrol-1-yl)benzaldehyde as a yellow oil; nmr (CDCl3,250 Mhz) dH 10.00 (CHO).

EXAMPLE 22

Reaction of 3-amino-5,5-dimethyl-2-cyclohexen-1-one with 4-chloro-3-phenylsulphonylbenzaldehyde dimethyl acetal in an analogous manner to that described in Example 1 gave 9-[3-benzenesulphonyl-4-chlorophenyl]-3,4,6,7,9,10-hexahydro-3,3,6,6-tetramethyl-1,8(2H,5H)-acridinedione. Crystallization from dimethylformamide/water gave a yellow crystalline solid of melting point 252–254° C. (decomposition).

The 4-chloro-3-phenylsulphonylbenzaldehyde dimethyl acetal used at the starting material was prepared as follows:

A suspension of 500 mg of 4-chloro-3-phenylthiobenzaldehyde dimethyl acetal (prepared as described in Example 12), 1.09 g of sodium metaperiodate, followed by a catalytic amount of ruthenium trichloride was stirred at room temperature for 12 hours under nitrogen in a solvent composed of 4 ml of water, 2 ml of acetonitrile and 2 ml of carbon tetrachloride. The mixture was partitioned between 25 ml of diethyl ether and 25 ml of water. The ether phase was washed with two 10 ml portions of saturated aqueous sodium bicarbonate followed by two 10 ml portions of brine and then dried over anhydrous magnesium sulphate. The solution was concentrated under reduced pressure to give 388 mg of 4-chloro-3-phenylsulphonyl benzaldehyde dimethyl acetal as a clear oil.

EXAMPLE 23

Reaction of 3-amino-5,5-dimethyl-2-cyclohexen-1-one with 3-(1-imidazolyl)-benzaldehyde dimethyl acetal in an analogous manner to that described in Example 1 gave 3,4,6,7,9,10-hexahydro-9-[3-(1-imidazolyl)-phenyl]-3,3,6,6-tetramethyl-1,8(2H,5H)-acridinedione. Crystallization from methanol/water gave a yellow crystalline solid of melting point 286–288° C.

The 3-(1-imidazolyl)-benzaldehyde dimethyl acetal used as the starting material was prepared as follows:

A solution of 296 mg of imidazole and 131 mg of sodium hydride (80% dispersion in mineral oil) in 2 ml of anhydrous dimethylformamide was stirred at room temperature for 1 hour under nitrogen. 1.0 g of 3-bromobenzaldehyde dimethyl acetal and 30 mg copper powder were then added and the mixture was stirred at 150–160° C. under nitrogen for 36 hours. The cooled mixture was diluted with 20 ml of water and extracted with four 25 ml portions of dichloromethane. The combined extracts were washed with two 25 ml portions of 25% aqueous ammonia, followed by two 25 ml portions of brine and then dried over anhydrous magnesium sulphate. The solution was concentrated under reduced pressure to give 0.75 g of 3-(1-imidazolyl)-benzaldehyde dimethyl acetal as a clear viscous oil.

EXAMPLE 24

3-Amino-5,5-dimethyl-2-cyclohexen-1-one was reacted with 3-(4-pyridyloxy)-benzaldehyde dimethyl acetal in an analogous manner to that described in Example 1 to give 3,4,6,7,9,10-hexahydro-3,3,6,6-tetramethyl-9-[3-(4-pyridyloxy)-phenyl]-1,8(2H,5H)-acridinedione. Purification by column chromatography on silica gel using dichloromethane/methanol (95:5) as the eluent gave a beige solid of melting point 186–188° C.

The 3-(4-pyridyloxy)-benzaldehyde dimethyl acetal used as the starting material was prepared as follows:

A solution of 1 g of 3-hydroxybenzaldehyde dimethyl acetal and 2 g of potassium tert.butoxide in 10 ml of anhydrous dimethylformamide was heated at 60° C. under an atmosphere of dry nitrogen for 1 hour. The mixture was then cooled to room temperature and 900 mg of 4-chloropyridinium hydrochloride were added portionwise over a period of 20 minutes. The mixture was then heated at 160° C. for 18 hours, cooled, 100 ml of water were added and the product was extracted with ethyl acetate. The combined extracts were washed with 1M aqueous sodium hydroxide solution and with brine, and then dried over anhydrous magnesium sulphate. Evaporation to dryness left a brown oil which was purified by column chromatography on silica gel using hexane/ethyl acetate (gradient: 90:10 to 20:80) for the elution to give 3-(4-pyridyloxy)-benzaldehyde dimethyl acetal as a light brown oil.

EXAMPLE 25

Reaction of 3-amino-5,5-dimethyl-2-cyclohexen-1-one with 4-chloro-3-(4-pyridyloxy)-benzaldehyde dimethyl acetal in an analogous manner to that described in Example 1 gave 9-[4-chloro-3-(4-pyridyloxy)-phenyl]-3,4,6,7,9,10-hexahydro-3,3,6,6-tetramethyl-1,8(2H,5H)-acridinedione. Crystallization from dimethylformamide water gave a yellow crystalline solid of melting point 242–244° C.

The 4-chloro-3-(4-pyridyloxy)-benzaldehyde dimethyl acetal used as the starting material was prepared in an analogous manner to that described in Example 24. Purification by column chromatography on silica gel using ethyl acetate/hexane (70:30) for the elution gave the product as a light yellow oil.

EXAMPLE 26

Reaction of 3-amino-5,5-dimethyl-2-cyclohexen-1-one with 3-(4-pyridylmethoxy)-benzaldehyde dimethyl acetal in an analogous manner to that described in Example 1 gave 9-[3-(4-pyridylmethoxy)-phenyl]-3,4,6,7,9,10-hexahydro-3,3,6,6-tetramethyl-1,8(2H,5H)-acridinedione. Crystallization from methanol/water gave a yellow crystalline solid of melting point 156–158° C.

The 3-(4-pyridylmethoxy)-benzaldehyde dimethyl acetal used at the starting material was prepared in an analogous manner to that described in Example 24. Purification by column chromatography on silica gel using ethyl acetate/hexane (70:30) for the elution gave the product as a colourless oil.

EXAMPLE 27

Reaction of 3-amino-5,5-dimethyl-2-cyclohexen-1-one with 3-(2-pyrazinyloxy)-benzaldehyde dimethyl acetal in an analogous manner to that described in Example 1 gave 3,4,6,7,9,10-hexahydro-3,3,6,6-tetramethyl-9- [3-(2-pyrazinyloxy)phenyl]-1,8-(2H,5H)-acridinedione. Crystallization from dimethylformamide/water gave a pale brown crystalline solid of melting point 204–207° C.

The 3-(2-pyrazinyloxy)-benzaldehyde dimethyl acetal used as the starting material was prepared as follows:

A solution of 168 mg of 3-hydroxybenzaldehyde dimethyl acetal in 10 ml of anyhydrous dimethylformamide was stirred under nitrogen and 220 mg of potassium tert-butoxide were added. The mixture was heated at 60° C. for 1 hour, then cooled to room temperature and 115 mg of 2-chloropyrazine were added in portions. The mixture was then heated at 160° C. for 18 hours. After cooling 15 ml of water were added and the product was extracted with 50 ml of ethyl acetate. The extract was washed with 25 ml of 1M sodium hydroxide solution and 25 ml of brine and then dried over anhydrous magnesium sulphate. After filtration and evaporation of the filtrate the residual yellow oil was purified by column chromatography on silica gel using ethyl acetate/hexane (1:1) for the elution to give 3-(2-pyrazinyloxy)-benzaldehyde dimethyl acetal as a yellow oil.

EXAMPLE 28

Reaction of 3-amino-5,5-dimethyl-2-cyclohexen-1-one with 3-(2-pyrimidinyloxy)-benzaldehyde dimethyl acetal in an analogous manner to that described in Example 1 gave 3,4,6,7,9,10-hexahydro-3,3,6,6-tetramethyl-9- [3-(2-pyrimidinyloxy)-phenyl]-1,8(2H,5H)-acridinedione. Crystallization from dimethylformamide/water gave a pale yellow crystalline solid of melting point 220–221° C.

The 3-(2-pyrimidinyloxy)-benzaldehyde dimethyl acetal used as the starting material was prepared as follows:

A solution of 168 mg of 3-hydroxybenzaldehyde dimethyl acetal in 2 ml of anhydrous dimethylformamide was stirred under nitrogen and 220 mg of potassium tert.butoxide were added. The mixture was heated at 60° C. for 1 hour, then cooled to room temperature and 114 mg of 2-chloropyrimidine were added in portions. The mixture was heated at 150° C. for 20 hours. After cooling 20 ml of water were added and the product was extracted with ethyl acetate. The extracts were washed with 10 ml of 1M sodium hydroxide solution and 5 ml of brine and then dried over anhydrous magnesium sulphate. After filtration and evaporation of the filtrate the residual brown gum was purified by column chromatography on silica gel using ethyl acetate/hexane (1:1) for the elution to give 3-(2-pyrimidinyloxy)-benzaldehyde dimethyl acetal as a syrup.

EXAMPLE 29

Reaction of 3-amino-5,5-dimethyl-2-cyclohexen-1-one with 4-nitro-3-benzyloxybenzaldehyde dimethyl acetal in an analogous manner to that described in Example 1, gave 9-(3-benzyloxy-4-nitrophenyl)-3,4,6,7,9,10-hexahydro-3,3,6,6-tetramethyl-1,8(2H,5H)-acridinedione. Crystallization from methanol/water gave a yellow crystalline solid of melting point 239–240° C.

The 4-nitro-3-benzyloxybenzaldehyde dimethyl acetal used as the starting material was prepared as follows:

A solution of 1.0 g of 4-nitro-3-hydroxybenzaldehyde dimethyl acetal and 212 mg of sodium hydride (80% dispersion in mineral oil) in 10 ml of anhydrous dimethyl formamide was stirred at 50° C. under nitrogen for 1 hour. A solution of 1.20 g of benzyl bromide dissolved in 10 ml of anhydrous dimethylformamide was added dropwise, followed by 174 mg of tetrabutylammonium iodide and the mixture was stirred at 60° C. under nitrogen for 48 hours.

The cooled mixture was concentrated under reduced pressure and the yellow oily residue dissolved in 150 ml of ethyl acetate, washed with four 25 ml portions of water, followed by two 25 ml portions of brine and then dried over anhydrous magnesium sulphate. The solution was evaporated to give 1.47 g of 4-nitro-3-benzyloxybenzaldehyde dimethyl acetal as a light yellow oil.

EXAMPLE 30

A solution of 57 mg of isonicotinic acid in 2.5 ml of anhydrous tetrahydrofuran was stirred under nitrogen and cooled to 5° C. in ice. To this solution were added 48 mg of 4-ethylmorpholine, 150 mg of 3,4,6,7,9,10-hexahydro-3,3,6,6-tetramethyl-9-(3-aminophenyl)-1,8(2H,5H)-acridinedione, 57 mg of 1-hydroxybenzotriazole and 80 mg of 1-(3-dimethylaminopropyl)-3-ethylcarbodiimide hydrochloride. The mixture was allowed to warm slowly to room temperature and then stirred for 18 hours. After evaporation of the solvent the residue was treated with 15 ml of water and extracted with ethyl acetate. The combined extracts were washed with saturated sodium hydrogen carbonate solution and brine and then dried over anhydrous magnesium sulphate. Filtration followed by evaporation of the filtrate gave a solid which was purified by column chromatography on silica gel using methanol/dichloromethane 1:9 for the elution to give 3,4,6,7,9,10-hexahydro-3,3,6,6-tetramethyl-9-[3-[(4-pyridyl)-carboxamido]-phenyl]-1,8 (2H,5H)-acridinedione as a pale yellow solid of melting point 295–297° C.

The 3,4,6,7,9,10-hexahydro-3,3,6,6-tetramethyl-9-(3-aminophenyl)-1,8(2H,5H)-acridinedione used as the starting material was prepared as follows:

(A) Reaction of 18.4 g of 3-amino-5,5-dimethyl-2-cyclohexen-1-one with 10 g of 3-nitrobenzaldehyde in an analogous manner to that described in Example 1 gave 3,4,6,7,9,10-hexahydro-3,3,6,6-tetramethyl-9-(3-nitrophenyl)-1,8-(2H,5H)-acridinedione. Crystallization from dimethylformamide/water gave 22.6 g of pure material as pale yellow crystals of melting point >280° C., (B) A solution of 10 g of 3,4,6,7,9,10-hexahydro-3,3,6,6-tetramethyl-9-(3-nitrophenyl)-1,8(2H,5H)-acridinedione in 190 ml of ethanol and 100 ml of 1M hydrochloric acid was hydrogenated at atmospheric temperature and pressure in the presence of 0.5 g of 10% palladium on carbon catalyst. When hydrogen uptake had ceased, the catalyst was removed by filtration and the filtrate evaporated. The residue was dissolved in water (20 ml) and the solution made alkaline by addition of excess 1M sodium carbonate solution. The precipitated solid was filtered off, washed with water and dried giving 9.0 g of 3,4,6,7,9,10-hexahydro- 3,3,6,6-tetramethyl-9-(3-aminophenyl)-1,8 (2H,5H)-acridinedione as a pale brown solid; mass spectrum (ESP) m/e 365 [M+H]+.

EXAMPLE 31

Reaction of 3-amino-5,5-dimethyl-1-one with 3-fluoro-4-trifluoromethylbenzaldehyde in an analogous manner to that described in Example 1 gave 9-[3-fluoro-4-trifluoromethylphenyl]-3,4,6,7,9,10-hexahydro-3,3,6,6-tetramethyl-1,8(2H,5H)-acridinedione. Crystallization from dimethylformamide/water gave a yellow crystalline solid of melting point 296–300° C.

EXAMPLE 32

Reaction of 3-amino-5,5-dimethyl-2-cyclohexen-1-one with 4-chloro-3-(4-pyridylthio)-benzaldehyde dimethyl acetal in an analogous manner to that described in Example 1 gave 9-[4-chloro-3-(4-pyridylthio)-phenyl-3,4,6,7,9,10-hexahydro-3,3,6,6-tetramethyl-1,8(2H,5H)-acridinedione. Mass spectrum (ESP) m/e 493 [M+H+].

The 4-chloro-3-(4-pyridylthio)-benzaldehyde dimethyl acetal used as starting material was prepared as follows:
(A) To a stirred solution of 10.0 g of 3-bromo-4-chlorobenzoic acid in 275 ml of anhydrous dichloromethane at 0° C. were added 7.6 g of 1-(3-dimethylaminopropyl)-3-ethylcarbodiimide hydrochloride and 5.5 ml of triethylamine followed by 3.9 g of N,O-dimethylhydroxylamine hydrochloride. After stirring overnight at room temperature the mixture was washed with 200 ml of water and then with 200 ml of a 1M solution of hydrochloric acid. The organic solution was dried over anhydrous sodium sulphate and concentrated under reduced pressure to give 10.7 g of 3-bromo-4-chloro-N-methoxy-N-methylbenzamide as a cream solid.
(B) A solution of 10.7 g of 3-bromo-4-chloro-N-methoxy-N-methylbenzamide in 100 ml of anhydrous tetrahydrofuran was added dropwise to 43 ml of a 1M solution of lithium aluminium hydride in tetrahydrofuran at below 5° C., and stirred for 1 hour. 100 ml of saturated ammonium chloride solution was then added cautiously followed by 100 ml of a 1M solution of hydrochloric acid and the mixture was extracted twice with 400 ml of diethyl ether. The combined organic extracts were dried over anhydrous sodium sulphate and concentrated under reduced pressure to give 6.8 g of 3-bromo-4-chlorobenzaldehyde as a pale yellow solid.
(C) A solution of 6.8 g of 3-bromo-4-chlorobenzaldehyde in 17 ml of trimethyl orthoformate was stirred with 6.9 g of Amberlyst 15 resin at room temperature overnight. The mixture was filtered and the filtrate was evaporated to give 4.5 g of 3-bromo-4-chlorobenzaldehyde dimethyl acetal as a colourless oil, mass spectrum (EI) m/e 266 [M+].
(D) A solution of 222 mg of 4-mercaptopyridine in 2 ml of anhydrous dimethylformamide was added dropwise to a suspension of 80 mg of a 60% dispersion of sodium hydride in mineral oil in 15 ml of anhydrous dimethylformamide at below 5° C. After 50 minutes a solution of 0.5 g of 3-bromo-4-chlorobenzaldehyde in 1 ml of anhydrous dimethylformamide was added dropwise and the mixture was heated at 150° C. for 29 hours. The mixture was then cooled to below 5° C. and 5 ml of a 1M solution of hydrochloric acid were added cautiously. The mixture was diluted with 50 ml of water and then extracted twice with 100 ml of ethyl acetate. The combined organic extracts were dried over anhydrous sodium sulphate, filtered and evaporated to dryness. The residue was purified by column chromatography on silica gel using methanol/dichloromethane (5:95) as the eluent to give 120 mg of 4-chloro-3-(4-pyridylthio)-benzaldehyde dimethyl acetal as a pale yellow oil, mass spectrum (CI) m/e 296 [M+].

The following Examples illustrate the preparation of other compounds of formula I:

EXAMPLE 33

5,5-Dimethyl-1,3-cyclohexanedione was reacted with 1,4-benzodioxan-6-carboxaldehyde in an analogous manner to that described in Example 2 to give 9-(1,4-benzodioxan-6-yl)-3,4,6,7,9,10-hexahydro-3,3,6,6-tetramethyl-1,8(2H,5H)-acridinedione. Recrystallization from dimethylformamide/water gave a yellow crystalline solid of melting point >300° C.

EXAMPLE 34

3-Amino-5,5-dimethyl-2-cyclohexen-1-one was reacted with 3-phenylbenzaldehyde in an analogous manner to that described in Example 1 to give 9-(3-biphenylyl)-3,4,6,7,9,10-hexahydro-3,3,6,6-tetramethyl-1,8(2H,5H)-acridinedione. Crystallization from ethanol gave a pale yellow crystalline solid of melting point 227–229° C.

EXAMPLE 35

3-Amino-5,5-dimethyl-2-cyclohexen-1-one was reacted with 3-phenoxybenzaldehyde in an analogous manner to that described in Example 1 to give 3,4,6,7,9,10-hexahydro-3,3,6,6-tetramethyl-9-(3-phenoxyphenyl)-1,8(2H,5H)-acridinedione. Crystallization from dimethylformamide/water gave a yellow crystalline solid of melting point 205–207° C.

EXAMPLE 36

3-Amino-5,5-dimethyl-2-cyclohexen-1-one was reacted with 3-phenylthiobenzaldehyde in an analogous manner to that described in Example 1 to give 3,4,6,7,9,10-hexahydro-3,3,6,6-tetramethyl-9-(3-phenylthiophenyl)-1,8(2H,5H)-acridinedione. Crystallization from dimethylformamide/water gave a yellow crystalline solid of melting point 252–253° C.

EXAMPLE 37

3-Amino-5,5-dimethyl-2-cyclohexen-1-one was reacted with 3-(4-methylphenoxy)benzaldehyde in an analogous manner to that described in Example 1 to give 3,4,6,7,9,10-hexahydro-3,3,6,6-tetramethyl-9-[3-(4-methylphenoxy)-phenyl]-1,8(2H,5H)-acridinedione. Crystallization from ethanol gave a pale yellow crystalline solid of melting point 202–203° C.

EXAMPLE 38

3-Amino-5,5-dimethyl-2-cyclohexen-1-one was reacted with 3-(4-methoxyphenoxy)-benzaldehyde in an analogous manner to that described in Example 1 to give 3,4,6,7,9,10-hexahydro-3,3,6,6-tetramethyl-9- [3-(4-methoxyphenoxy)-phenyl]-1,8(2H,5H)-acridinedione. Crystallization from ethanol/water gave a pale yellow crystalline solid of melting point 210–212° C.

EXAMPLE 39

3-Amino-5,5-dimethyl-2-cyclohexen-1-one was reacted with 3-(3,5-dichlorophenoxy)-benzaldehyde in an analogous manner to that described in Example 1 to give 9-[3-(3,5-dichlorophenoxy)-phenyl]-3,4,6,7,9,10-hexahydro-3,3,6,6-tetramethyl-1,8(2H,5H)-acridinedione. Crystallization from dimethylformamide/water gave a yellow crystalline solid of melting point 254–255° C.

EXAMPLE 40

3-Amino-5,5-dimethyl-2-cyclohexen-1-one was reacted with 3-(4-chlorophenoxy)benzaldehyde in an analogous manner to that described in Example 1 to give 9-[3-(4-chlorophenoxy)-phenyl]-3,4,6,7,9,10-hexahydro-3,3,6,6- tetramethyl-1,8(2H,5H)-acridinedione. Crystallization from dimethylformamide/water gave a beige crystalline solid of melting point 238–239° C.

EXAMPLE 41

Reaction of 5,5-dimethyl-1,3-cyclohexanedione with 4-trifluoromethoxybenzaldehyde in an analogous manner to that described in Example 2, except that the reaction time following addition of the aldehyde was 5 days. This gave 9-(4-trifluoromethoxy-phenyl)-3,4,6,7,9,10-hexahydro-3,3,6,6-tetramethyl-1,8(2H,5H)-acridinedione, which formed a yellow crystalline solid of melting point 234° C. after crystallization from ethanol.

EXAMPLE 42

Reaction of 5,5-dimethyl-1,3-cyclohexanedione with 4-cyanobenzaldehyde in an analogous manner to that described in Example 2 gave 4-(2,3,4,5,6,7,8,9-octahydro-3,3,6,6-tetramethyl-1,8-dioxo-1H-acridin-9-yl)benzonitrile. Crystallization from dimethylformamide/water gave yellow-green solid of melting point >300° C. (decomposition).

EXAMPLE 43

3-Amino-5,5-dimethyl-2-cyclohexen-1-one was reacted with 2-bromobenzaldehyde in an analogous manner to that described in Example 1 to give 9-(2-bromophenyl)-3,4,6,7,9,10-hexahydro-3,3,6,6-tetramethyl-1,8(2H,5H)-acridinedione. Crystallization from dimethylformamide/water gave a yellow powder of melting point >285° C. (decomposition).

EXAMPLE 44

3-Amino-5,5-dimethyl-2-cyclohexen-1-one was reacted with 3-benzoyloxybenzaldehyde in an analogous manner to that described in Example 1 to give 9-(3-benzoyloxyphenyl)-3,4,6,7,9,10-hexahydro-3,3,6,6-tetramethyl-1,8(2H,5H)-acridinedione. Crystallization from ethanol gave a pale yellow crystalline solid of melting point 274–275° C. (decomposition).

EXAMPLE 45

3-Amino-5,5-dimethyl-2-cyclohexen-1-one was reacted with 3-benzyloxybenzaldehyde in an analogous manner to that described in Example 1 to give 9-(3-benzyloxyphenyl)-3,4,6,7,9,10-hexahydro-3,3,6,6-tetramethyl-1,8(2H,5H)-acridinedione. Crystallization from ethanol gave a cream coloured crystalline solid of melting point >300° C. (decomposition).

EXAMPLE 46

Reaction of 5,5-dimethyl-1,3-cyclohexanedione with naphthalene-2-carboxaldehyde in an analogous manner to that described in Example 2 gave 3,4,6,7,9,10-hexahydro-3,3,6,6-tetramethyl-9-(2-naphthyl)-1,8-(2H,5H)-acridinedione. Crystallization from methanol to give a cream coloured powder of melting point >300° C.

EXAMPLE 47

3-Amino-5,5-dimethyl-2-cyclohexen-1-one was reacted with pyridine-4-carboxaldehyde in an analogous manner to that described in Example 1 to give 3,4,6,7,9,10-hexahydro-3,3,6,6-tetramethyl-9-(4-pyridyl)-1,8(2H,5H)-acridinedione. Crystallization from dimethylformamide/water gave a pale yellow crystalline solid of melting point 218–219° C. (decomposition).

EXAMPLE 48

3-Amino-5,5-dimethyl-2-cyclohexen-1-one was reacted with 5-methyl-2-thiophenecarboxaldehyde in an analogous manner to that described in Example 1 to give 3,4,6,7,9,10-hexahydro-3,3,6,6-tetramethyl-9-(5-methyl-2-thienyl)-1,8(2H,5H)-acridinedione. Crystallization from ethyl acetate/methanol gave a beige crystalline solid of melting point 266–268° C. (decomposition).

EXAMPLE 49

3-Amino-5,5-dimethyl-2-cyclohexen-1-one was reacted with 5-nitro-furfuraldehyde in an analogous manner to that described in Example 1 to give 3,4,6,7,9,10-hexahydro-3,3,6,6-tetramethyl-9-(5-nitro-2-furyl)-1,8(2H,5H)-acridinedione. Crystallization from ethyl acetate/methanol gave a beige crystalline solid of melting point 248–250° C. (decomposition).

EXAMPLE 50

A solution of 980 mg of 5,5-dimethyl-1,3-cyclohexanedione, 550 mg of 5-nitro-2-thiophenecarboxaldehyde and 7 mg of p-toluenesulphonic acid in 70 ml of toluene were heated at reflux for 90 minutes. The mixture was evaporated to dryness and the residue was crystallized from ethyl acetate to give 3,4,6,7,9,10-hexahydro-3,3,6,6-tetramethyl-9-(5-nitro-2-thienyl)-1H-xanthene-1,8(2H)-dione as a yellow crystalline solid of melting point 298–300° C.

EXAMPLE 51

A slurry of 17 mg of sodium hydride (80% dispersion in mineral oil) in 10 ml of anhydrous tetrahydrofuran was stirred at room temperature under an atmosphere of dry nitrogen and treated dropwise with a solution of 200 mg of 3,4,6,7,9,10-hexahydro-3,3,6,6-tetramethyl-9-(4-nitrophenyl)-1,8(2H,5H)-acridinedione in 5 ml of dimethylformamide. The mixture was then heated at reflux for 15 minutes, cooled to room temperature, treated with 44 ml of methyl chloroformate and stirred at room temperature under an atmosphere of dry nitrogen for 18 hours. The solvents were removed under reduced pressure and the resulting waxy residue was taken up in diethyl ether and the insoluble material was filtered off. The filtrate was then purified by column chromatography on silica gel using hexane/ethyl acetate (gradient: 80:20 to 50:50) as the eluent to give methyl 2,3,4,5,6,7,8,9-octahydro-3,3,6,6-tetramethyl-9-(4-nitrophenyl)-1,8-dioxo-1H-acridine-10-carboxylate as a white crystalline solid of melting point 189–190° C.

EXAMPLE 52

A solution of 1.39 g of 3-amino-5,5-dimethyl-2-cyclohexen-1-one, 1.26 g of 5-methyl-cyclohexane-1,3-dione and 1.51 g of 4-bromobenzaldehyde in 18 ml of absolute ethanol and 6 ml of glacial acetic acid was heated under reflux under a nitrogen atmosphere for 12 hours. The mixture was then cooled to room temperature and about 10 ml of water was added until the product precipitated. The product was filtered off and washed with three 50 ml portions of cold diethyl ether to give 9-(4-bromophenyl)-3,4,6,7,9,10-hexahydro-3,3,6(RS)-trimethyl-1,8(2H,5H)-acridinedione as a pale yellow solid. The product was shown to be a 9:1 mixture of diastereoisomers by HPLC and gave a mass ion of 414 (FAB, [M+H]+).

EXAMPLE 53

5-Methyl-cyclohexane-1,3-dione was reacted with 4-bromobenzaldehyde in an analogous manner to that described in Example 2 to give 9-(4-bromophenyl)-3,4,6,7,9,10-hexahydro-3,6-dimethyl-1,8(2H,5H)-acridinedione as a white crystalline solid. The product was shown by HPLC to be a mixture of 3 diastereoisomers and gave a mass ion of 401 (FAB, [M+H]+).

EXAMPLE 54

5-Ethyl-cyclohexane-1,3-dione was reacted with 4-bromobenzaldehyde in an analogous manner to that described in Example 2 to give 9(RS)-(4-bromophenyl)-3(RS),6(RS)-diethyl-3,4,6,7,9,10-hexahydro-1,8(2H,5H)-acridinedione as a white crystalline solid. The product was shown by HPLC to be a mixture of 3 diastereoisomers and gave a mass ion of 428 ([FAB, [M+H]+).

EXAMPLE 55

5-Isopropyl-cyclohexane-1,3-dione was reacted with 4-bromobenzaldehyde in an analogous manner to that described in Example 2 to give 9(RS)-(4-bromophenyl)-3(RS),6(RS)-diisopropyl-3,4,6,7,9,10-hexahydro-1,8(2H,5H)-acridinedione as a white crystalline solid. The product was shown by HPLC to be a mixture of 3 diastereoisomers and gave a mass ion of 456 [FAB, [M+H]+).

The following Example illustrates a pharmaceutical preparation containing a compound of formula I.

EXAMPLE A

Tablets containing the following ingredients may be produced in a conventional manner:

|  |  |
| --- | --- |
| Compound of formula I | 100 mg |
| Lactose | 70 mg |
| Corn starch | 70 mg |
| Polyvinylpyrrolidone | 5 mg |
| Magnesium stearate | 5 mg |
| Tablet weight | 250 mg |

We claim:

1. A dione selected from the group consisting of compounds of the formula:

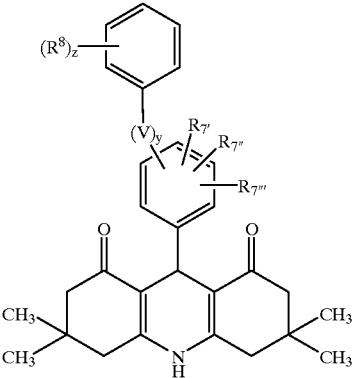

I-A₁ wherein V is —O—, —CH$_2$O— or —S—; R$_{7'}$, R$_{7''}$, R$_{7'''}$ and R$^8$ are individually halo, lower alkyl, hydrogen, halo-lower alkyl, lower alkoxy or nitro; with the proviso that one of R$_{7'}$, R$_{7''}$ or R$_{7'''}$ is other than hydrogen; z is an integer from 0 to 3; and y is an integer from 0 to 1;

and a salt thereof.

2. The dione of claim 1 wherein V is —O— and y is 1.

3. The dione of claim 1 wherein said compound is 9-(4-chloro-3-phenoxyphenyl)-3,4,6,7,9,10-hexahydro-3,3,6,6-tetramethyl-1,8(2H,5H)-acridinedione.

4. The dione of claim 1 wherein V is —CH$_2$O— and y is 1.

5. The dione of claim 4 wherein said compound is 9-(3-benzyloxy-4-nitrophenyl)-3,4,6,7,8,10-hexahydro-3,3,6,6-tetramethyl-1,8(2H,5H)-acridinedione.

6. The dione of claim 1 wherein y is 0.

7. The dione of claim 6 wherein said compound is 9-(6-chloro-3-biphenylyl)-3,4,6,7,9,10-hexahydro-3,3,6,6-tetramethyl-1,8(2H,5H)-acridinedione.

8. The dione of claim 1 wherein y is 1 and V is —S—.

9. The dione in claim 8 wherein said compound is 9-(4-chloro-3-phenylthiophenyl)-3,4,6,7,9,10-hexahydro-3,3,6,6-tetramethyl-1,8(2H,5H)-acridinedione.

* * * * *